(12) United States Patent
Mire et al.

(10) Patent No.: US 9,131,933 B2
(45) Date of Patent: Sep. 15, 2015

(54) SURGICAL RETRACTOR AND METHOD OF USE

(71) Applicant: Warsaw Orthopedic, Inc., Warsaw, IN (US)

(72) Inventors: David A. Mire, Cordova, TN (US);
Paula A. Nichter, Memphis, TN (US);
Paul Wheeler, Hernando, MS (US);
Jacob Zimmerman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 195 days.

(21) Appl. No.: 13/875,036

(22) Filed: May 1, 2013

(65) Prior Publication Data

US 2014/0330086 A1 Nov. 6, 2014

(51) Int. Cl.
*A61B 17/02* (2006.01)

(52) U.S. Cl.
CPC ............. *A61B 17/0218* (2013.01); *A61B 17/02* (2013.01)

(58) Field of Classification Search
CPC ............................ A61B 17/0218; A61B 17/02
USPC .................................................. 600/201–246
See application file for complete search history.

(56) References Cited

U.S. PATENT DOCUMENTS

| | | | |
|---|---|---|---|
| 3,384,077 A | 5/1968 | Gauthier | |
| 3,384,078 A | 5/1968 | Gauthier | |
| 3,749,088 A | 7/1973 | Kohlmann | |
| 4,616,635 A * | 10/1986 | Caspar et al. | 600/215 |
| 5,746,743 A | 5/1998 | Greenberg | |
| 5,928,139 A | 7/1999 | Koros et al. | |
| 6,139,493 A * | 10/2000 | Koros et al. | 600/215 |
| 6,808,493 B1 | 10/2004 | Bookwalter et al. | |
| 7,491,168 B2 | 2/2009 | Raymond et al. | |
| 2004/0260246 A1* | 12/2004 | Desmond | 604/174 |
| 2005/0137461 A1 | 6/2005 | Marchek et al. | |
| 2006/0287584 A1 | 12/2006 | Garcia-Bengochia | |
| 2007/0208228 A1 | 9/2007 | Pavento et al. | |
| 2008/0188718 A1 | 8/2008 | Spitler et al. | |
| 2009/0018400 A1 | 1/2009 | Raymond et al. | |
| 2009/0105547 A1 | 4/2009 | Vayser et al. | |
| 2011/0021880 A1* | 1/2011 | Okoniewski | 600/215 |
| 2013/0096387 A1* | 4/2013 | DeRidder et al. | 600/214 |

* cited by examiner

*Primary Examiner* — Christopher Beccia
(74) *Attorney, Agent, or Firm* — Sorell Lenna & Schmidt LLP

(57) ABSTRACT

A retractor includes a first wall extending from the base. The first wall has a longitudinal axis and extends between a first end and a second end. The first wall includes at least a portion of a longitudinal cavity. A rotatable shaft includes an outer surface that defines a groove. At least a portion of the shaft is disposed in the longitudinal cavity. A blade is disposed for movement along the longitudinal cavity. A post is connected with the blade and is disposed with the groove such that rotation of the shaft causes axial translation of the blade relative to the first wall between a first orientation and a second orientation. Methods of use are disclosed.

13 Claims, 6 Drawing Sheets

SURGICAL RETRACTOR AND METHOD OF USE

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

Accordingly, a surgical system and method are provided for accessing a surgical site, which may include, for example, a portion of a spine to facilitate treatment thereof. It is contemplated that the surgical system and method may be employed for exposing and providing a surgical pathway to a surgical site.

In one embodiment, in accordance with the principles of the present disclosure, a retractor is provided. The retractor includes a base. A first wall extends from the base. The first wall has a longitudinal axis and extends between a first end and a second end. The first wall includes at least a portion of a longitudinal cavity. A rotatable shaft includes an outer surface that defines a groove. At least a portion of the shaft is disposed in the longitudinal cavity. A blade is disposed for movement along the longitudinal cavity. A post is connected with the blade and is disposed with the groove such that rotation of the shaft causes axial translation of the blade relative to the first wall between a first orientation and a second orientation.

In one embodiment, the retractor comprises a base for connecting to a frame. A first wall extends from the base. The first wall defines a longitudinal axis. The wall extends between a first end and a second end. The wall defines a first longitudinal cavity extending between the first end and the second end and a second cavity disposed at the first end. A shaft includes an outer surface that defines a helical groove. The shaft includes a head for disposal in the second cavity. At least a portion of the shaft is disposed in the longitudinal cavity. A blade is connected with a pin to the shaft and is disposed for axial translation along the longitudinal cavity. The blade defines a second longitudinal cavity configured for disposal of the shaft. The pin is connected with the groove such that rotation of the shaft causes axial translation of the blade relative to the first extension between a first orientation and a second orientation such that the blade extends beyond the second end. The shaft includes a first lock surface engagable with a second lock surface of the base to releasably lock the blade in a selected dimension relative to the second end in the second orientation.

In one embodiment, the retractor comprises a base for connecting to a frame. A first tubular wall extends from the base. The first wall defines an inner surface defining an inner cavity and a longitudinal axis. The first wall extends between a first end and a second end. The first wall defines a longitudinal cavity recessed from the inner surface and extending between the first and second ends. A second cavity is disposed at the first end. A rotatable shaft includes an outer surface defining a groove. At least a portion of the shaft is disposed in the longitudinal cavity. The shaft includes a head for disposal in the second cavity. A pin is connected with the groove such that rotation of the shaft causes axial translation of the blade relative to the first wall between a first orientation and a second orientation such that the blade extends beyond the second end. A tubular blade is disposed concentrically with the first wall and connected with the pin. The blade is disposed for axial translation along the longitudinal cavity and the blade defines an outer surface that defines a second longitudinal cavity recessed from the outer surface and configured for disposal of the shaft.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
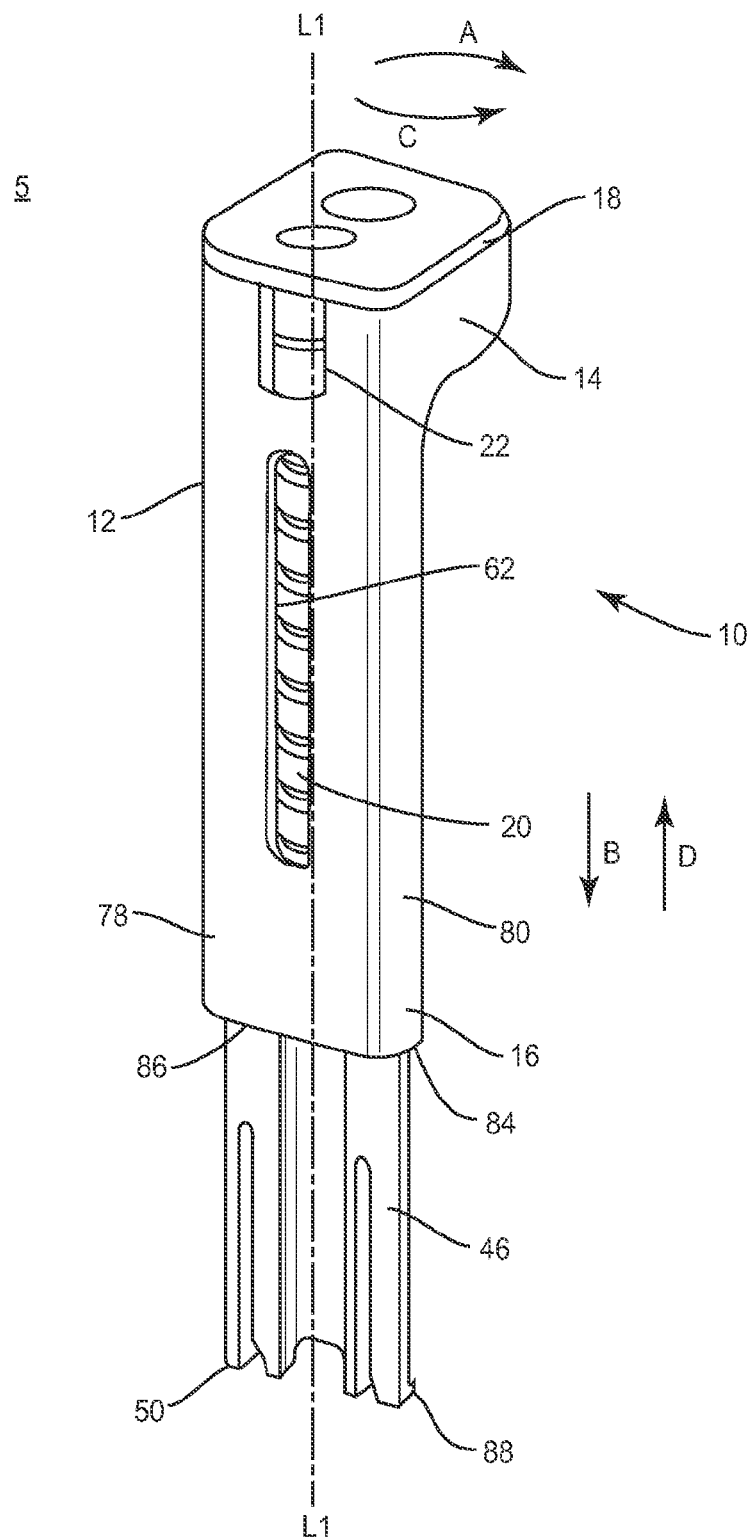
FIG. 1 is a perspective view of one embodiment of components of a system in accordance with the principles of the present disclosure.

The exemplary embodiments of the surgical system and related methods of use disclosed are discussed in terms of medical devices for the treatment of musculoskeletal disorders and more particularly, in terms of a surgical system for accessing a spine to facilitate treatment thereof and a method for treating a spine. The surgical system and methods presently disclosed provide facile assembly of a retractor system for connection of the mating parts. One or all of the system components may be reusable or disposable. The surgical system may be configured as a kit with multiple sized and configured components.

In one embodiment, the system includes a retractor having adjustable length retractor blades that are adjustable according to the requirements of a particular application. It is envisioned that the adjustable blades avoid tissue creep about the blade and into a surgical site. In one embodiment, the retractor comprises extendable blades that more closely mimic the anatomy and prevents tissue progression in the workspace. It is contemplated that the blades avoid undesired tissue creep into the workspace and/or tissue damage such as, for example, of the lungs, bowels or other anatomy. In one embodiment, the system includes a retractor having retractable blades. In one embodiment, the system includes a retractor that is configured as a tissue guard.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
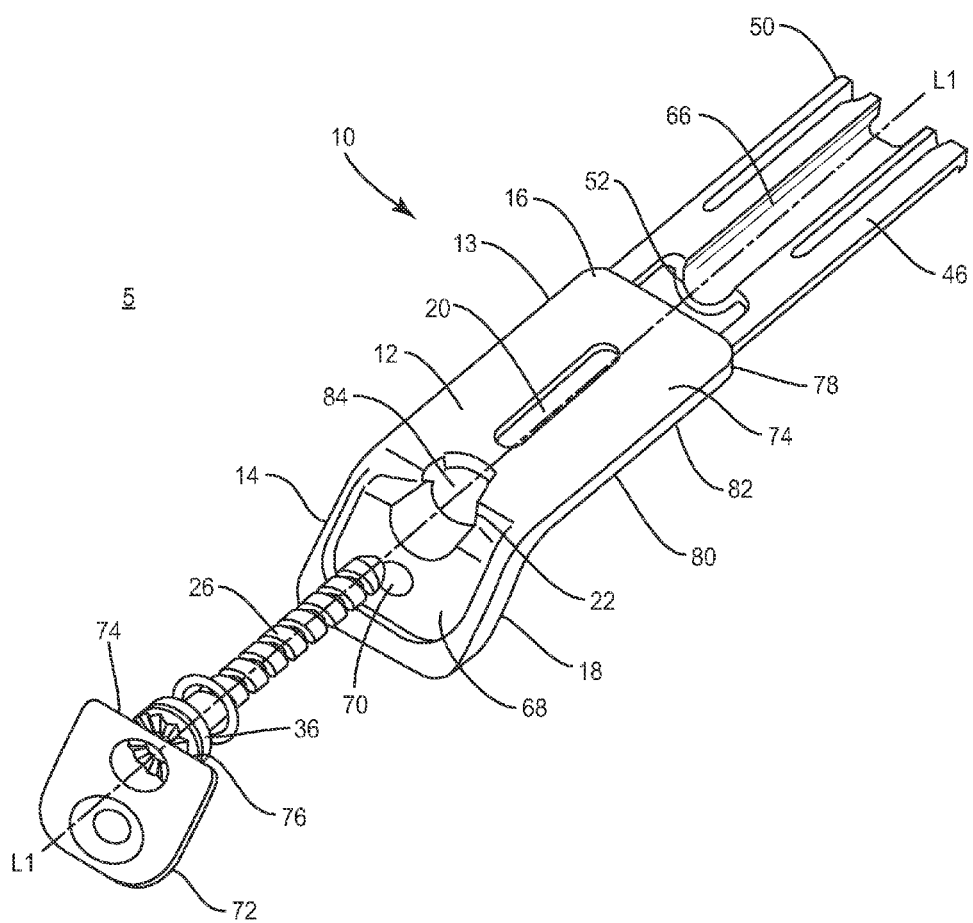
FIG. 2 is a perspective view of the components shown in FIG. 1.
Figure 3:
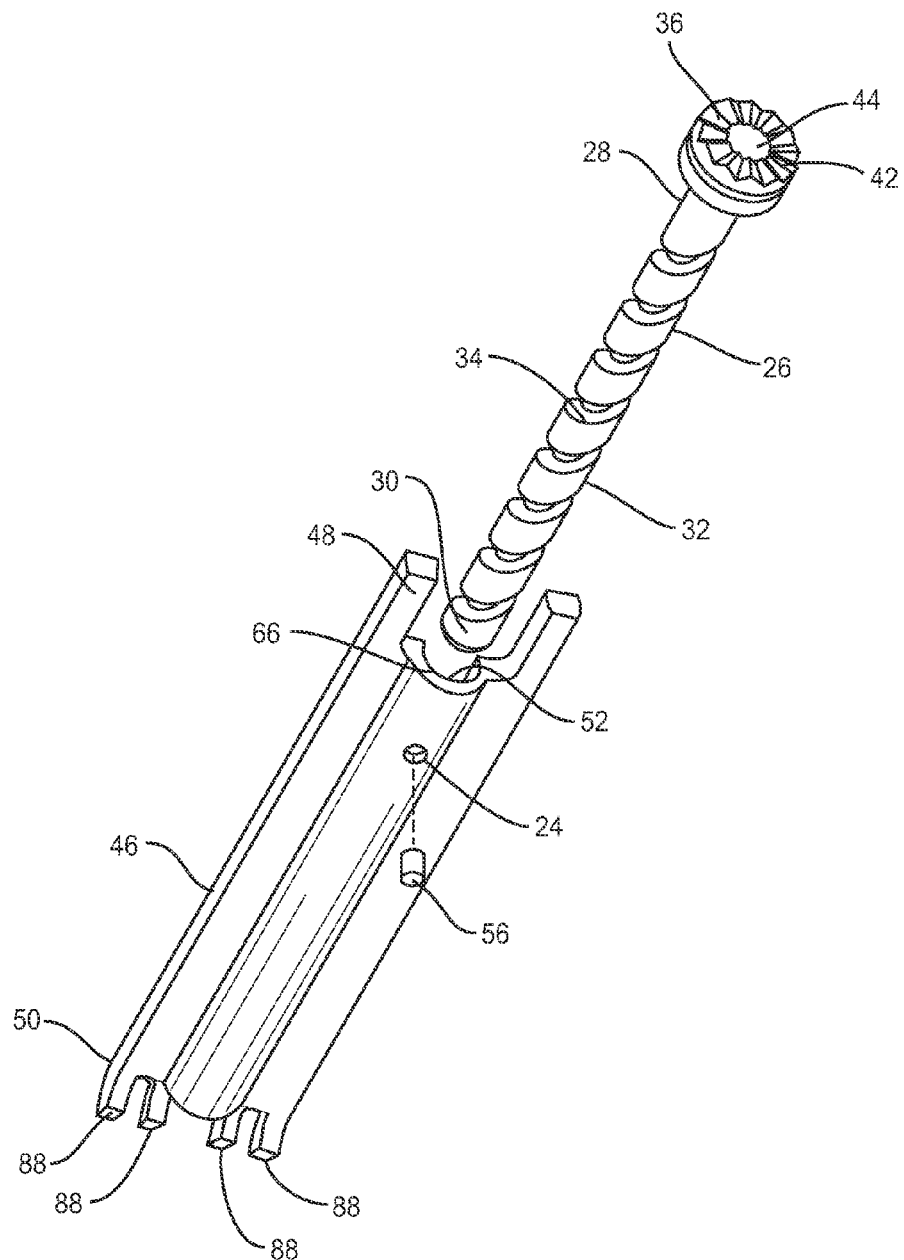
FIG. 3 is a perspective view of the components shown in FIG. 1 with parts separated.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there is illustrated components of a surgical system 5 including a retractor for accessing a spine to facilitate treatment thereof in accordance with the principles of the present disclosure.

The components of surgical system 5 can be fabricated from biologically acceptable materials suitable for medical applications, including metals, synthetic polymers, ceramics and/or their composites, depending on the particular application and/or preference of a medical practitioner. For example, the components of surgical system 5, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, composites of PEEK and calcium based ceramics, and composites of PEEK with resorbable polymers. Various components of surgical system 5 may have material composites, including the above materials, to achieve various desired characteristics such as strength, rigidity, elasticity, compliance, biomechanical performance, durability and radiolucency or imaging preference. The components of surgical system 5, individually or collectively, may also be fabricated from a heterogeneous material such as a combination of two or more of the above-described materials. The components of surgical system 5 may be monolithically formed, integrally connected or include fastening elements and/or instruments, as described herein.

Surgical system 5, is employed, for example, with minimally invasive, mini-open and/or open procedures for supporting tissue and/or anatomical structures to expose tissue and/or anatomical structures to create a surgical pathway and provide access to a surgical site, which includes, for example, a spine to facilitate treatment.

Surgical system 5 includes a retractor assembly 10 having a first wall, such as, for example, an extension 12 extending between a first end 14 and a second end 16. First end 14 includes a base 18 configured for attachment to a retractor frame (not shown). The frame allows for proper positioning and docking of retractor assembly 10 with an anatomy in alignment with the surgical site. It is contemplated that base 18 may be monolithically formed, integrally connected and/or include fastening elements that attach base 18 with the frame. In one embodiment, retractor assembly 10 may be employed with a free hand surgical technique such that base 18 is not connected to a frame.

Base 18 includes an inner surface 68 defining a cavity 70. Inner surface 68 is recessed from the outer surface of base 18 such that cavity 70 is configured for disposal of a cap 72. Cap 72 snaps into engagement with cavity 70. Cap 72 includes a bottom surface 74 defining a spline surface 76 for engagement with shaft 26, as discussed below.

Extension 12 defines a longitudinal axis L1. In one embodiment, the length of extension 12 is such that first end 14 is mounted to an external surface of a body and second end 16 engages tissue adjacent a surgical site. In one embodiment, all or only a portion of extension 12 can extend in an arcuate configuration relative to L1.

Extension 12 includes an outer wall section 78 and an inner wall section 80. Inner wall section 80 defines an inner surface 62. Inner surface 62 defines a portion of a longitudinal cavity, such as, for example, an elongated passageway 20 configured for disposal of a shaft 26, as discussed herein. Passageway 20 extends a length of extension 12 between and/or including first end 14 and second end 16 to facilitate relative axial translation of blade 46 into and out of extension 12. It is contemplated that inner surface 62 includes various surface configurations, such as, for example, smooth, rough, mesh, porous, semi-porous, dimpled and/or textured according to the requirements of a particular application.

Extension 12 includes an interior surface 13 that defines a passageway 84. Passageway 84 is configured for axial slidable disposal of blade 46 relative to extension 12. Extension 12 has an oblong cross-section to support the configuration of blade 46. It is contemplated that extension 12 may be tubular, cylindrical, elliptical or otherwise circular or non-circular in cross-section. Inner wall section 80 defines a second cavity 22 having an inner surface 82. Second cavity 22 is disposed at first end 14 and is configured for disposal of a portion of a head 36 of shaft 26, as discussed herein.

Second end 16 defines an opening 86 that communicates with passageway 84. Opening 86 has an oblong cross section and is configured to facilitate extension from and/or retraction of blade 46 into passageway 84. It is contemplated that opening 86 may be tubular, cylindrical, elliptical or otherwise circular or non-circular in cross-section.

A rotatable shaft 26 is configured for disposal in passageway 20. Shaft 26 extends between a first end 28 and a second end 30 along longitudinal axis L1. Shaft 26 has a cylindrical cross section and includes an outer surface 32 that defines a groove 34. Groove 34 defines a helical thread form. It is contemplated that the thread form can be linear, a single thread turn or a plurality of discrete threads.

Head 36 is disposed at first end 28 and is configured for disposal in second cavity 22. Head 36 defines a spline surface 42 configured for engagement with spline surface 76 of cap 72. Head 36 includes a socket 44 for engagement with a tool, such as, for example, a driver (not shown) to facilitate rotation of shaft 26 in a clockwise direction, as shown by arrow A in FIG. 1 or in a counter clockwise direction, as shown by arrow C. Shaft 26 rotates relative to inner surface 82 to axially translate blade 46 between a first orientation and a second orientation, as described. As the driver rotates shaft 26, head 36 rotates. In one embodiment, spline surfaces 42 and 76 engage to provide an indexed movement of blade 46 to selectively dispose blade 46 between the first orientation and the second orientation.

In one embodiment, spline surfaces 42, 76 are disposable in a splined mating geometry such that blade 46 can be locked in a position, in a first orientation and/or a second orientation, as described, relative to extension 12. The splined mating geometry includes spline surface 42 having teeth that are configured to engage teeth of spline surface 76. In a non-locking configuration, the teeth of splines 42, 76 are relatively rotatable to facilitate relative rotation of head 36 and cap 72. A biasing member, such as, for example, a spring (not shown) is disposed in second cavity 22 and is configured to force the teeth of spline surface 42 into engagement with the teeth of spline surface 76 to lock blade 46 in a selected position. Upon desired positioning of blade 46 relative to extension 12, splines 42, 76 are actuated for disposal of blade 46 in a locked configuration. The teeth of splines 42, 76 are driven into fixed engagement via the spring. This configuration locks position and orientation of head 36 relative to cap 72, and thereby prevents further rotation of shaft 26. As such, blade 46 is locked and/or fixed in a selected position relative to extension 12. Rotation of shaft 26 with a driver can overcome the engagement of spline surfaces 42, 76, as facilitated by the spring, to allow shaft 26 to be rotated for adjustment of blade 46.

Blade 46 extends between a first end 48 and a second end 50. Blade 46 is configured for axial translation along passageway 84 relative to extension 12 and shaft 26. Blade 46 includes an outer surface 66 that defines a portion of a passageway 20 configured for disposal of shaft 26. Blade 46 includes a lateral opening 24 for disposal of a pin 56 therein, as discussed herein. Blade 46 includes at least one foot 88 at its second end 50. Feet 88 are disposed transverse to longitudinal axis L1 and extend outwardly from second end 50 to engage tissue. Feet 88 are disposed in a spaced apart configuration and define gaps therebetween. It is contemplated that retractor assembly 10 may include one or a plurality of blades. It is envisioned that the blades may be oriented in alternate configurations, such as, for example, perpendicular, parallel, co-axial, angularly offset, offset and/or staggered relative to longitudinal axis L1.

It is further envisioned that all or only a portion of the surface of second end 50 may have alternate surface configurations, such as, for example, rough, threaded for connection with other instruments, arcuate, undulating, porous, semi-porous, dimpled, polished and/or textured according to the requirements of a particular application.

A post, such as, for example, a pin 56 is connected with blade 46 through lateral opening 24. Pin 56 remains fixed within opening 24 as shaft 26 rotates. As shaft 26 rotates, groove 34 moves along pin 56 driving pin 56 and blade 46 in at least one axial direction such that blade 46 translates relative to extension 12. Rotation of shaft 26 causes axial translation of blade 46 relative to extension 12 between the first orientation and the second orientation, as described herein. In one embodiment, pin 56 is biased into engagement with groove 34 via a spring (not shown). It is contemplated that the post may alternatively comprise a screw, nail, bit, clip and/or tab.

In one embodiment, the first orientation includes blade 46 being disposed within passageway 84 and second end 50 of blade 46 being disposed adjacent second end 16 of extension 12. Pin 56 is disposed adjacent to first end 28 of shaft 26. As shaft 26 is rotated, pin 56 moves along groove 34 such that blade 46 axially translates blade 46 to the second orientation, which includes various alternate positions of second end 50 relative to extension 12. In one embodiment, the second orientation includes a configuration such that second end 50 of blade 46 extends beyond second end 16 of extension 12. First end 48 of blade 46 is disposed adjacent second end 16 of extension 12. Pin 56 is disposed adjacent to second end 30 of shaft 26. It is envisioned that blade 46 may be disposed in one or a plurality of relative positions extending from extension 12 in the second orientation. It is further envisioned that such positions may include a range of displacement of second end 50 relative to second end 16, and/or may include increments of 1 centimeter.

In one embodiment, blade 46 is selectively positioned in the second orientation and blade 46 is locked in a selected dimension relative to second end 16. In one embodiment, shaft 26 includes a first lock surface, such as, for example, a cavity (not shown) that mates in receivable engagement with a second lock surface, such as, for example, a pin (not shown) of extension 12 to releasably lock second end 50 of blade 46 a selected dimension and/or distance relative to extension 12 in the second orientation. The pin is engageable for disposal in the cavity upon rotation of shaft 26 to axially translate blade 46 to a selective position corresponding to the selected dimension and/or distance.

In one embodiment, the first lock surface includes an outer friction surface of pin 56 and the second lock surface includes an outer friction surface of groove 34. Blade 46 is disposable in a fixed position relative to extension 12 such that the friction surfaces of pin 56 and groove 34 engage in releasable fixation to releasably lock second end 50 in a selected dimension and/or distance from second end 12 in the second orientation. Rotation of shaft 26 overcomes the frictional engagement of the friction surfaces of pin 56 and groove 34 to release fixation and the locked orientation of blade 46. Blade 46 freely translates during rotation of shaft 26.

In assembly, operation and use, as shown in FIGS. 1-3, surgical system 5, similar to that described, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

Retractor assembly 10 is positioned adjacent the surgical site over the small incision. Retractor assembly 10 is passed through the incision to create a passageway or portal to the surgical site. Blade 46 is disposed in the first orientation, as described.

To extend blade 46 to one or a plurality of positions corresponding to a second orientation, a driver, not shown, is engaged with socket 44 of head 36 to rotate shaft 26 in a first direction, such as, for example, a clockwise direction, as shown by arrow A in FIG. 1. Rotation of shaft 26 in the direction shown by arrow A causes blade 46 to axially translate along longitudinal axis L1, in the direction shown by arrow B. Blade 46 is selectively translatable between the first orientation and the second orientation. In the first orientation, blade 46 is disposed such that second end 50 is disposed adjacent second end 16 of extension 12. Pin 56 is disposed adjacent to second end 30 of shaft 26. As shaft 26 is rotated, pin 56 moves along groove 34 such that blade 46 axially translates to one or a plurality of positions corresponding to a selected second orientation.

Rotating shaft 26 engages pin 56 with groove 34 and pin 56 slides along groove 34 allowing for controlled movement of shaft 26 and blade 46. When blade 46 is disposed in a second orientation, first end 48 of blade 46 is disposed adjacent second end 16 of extension 12. The second orientation is such that second end 50 of blade 46 is extended beyond second end 16 of extension 12 at a selected dimension and/or distance, according to the requirements of a particular application. First end 48 of blade 46 is disposed adjacent second end 16 of extension 12. Pin 56 is disposed adjacent to first end 28 of shaft 26.

Blade 46 and feet 88 engage tissue to separate tissue adjacent the surgical site and/or prevent tissue from entering the passageway or portal at the surgical site and/or prevent tissue creep at the surgical site. In one embodiment, blade 46 can be locked in one or a plurality of first orientations, second orientations and/or a selected distance or dimension relative to extension 12, as described. Blade 46 can be disposed in orientations between the first and second orientation, as required by the procedure by rotation of shaft 26.

Upon completion of the procedure, blade 46 is axially translatable to a position within extension 12. Shaft 26 is rotated in a counter clockwise direction, as shown by arrow C. Rotation of shaft 26 in the direction shown by arrow C axially translates blade 46 in an axial direction, as shown by arrow D. Blade 46 translates from the second orientation to the first orientation such that blade 46 is drawn within extension 12. Retractor assembly 10 is removed from the surgical site. In one embodiment, retractor assembly 10 is removed from the surgical site while disposed in a second orientation.

It is envisioned that the use of microsurgical and image guided technologies may be employed to access, view and repair spinal deterioration or damage, with the aid of retractor assembly 10. It is contemplated that a surgical procedure may employ other instruments that can be mounted with retractor assembly 10, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Retractor assembly 10 may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 4:
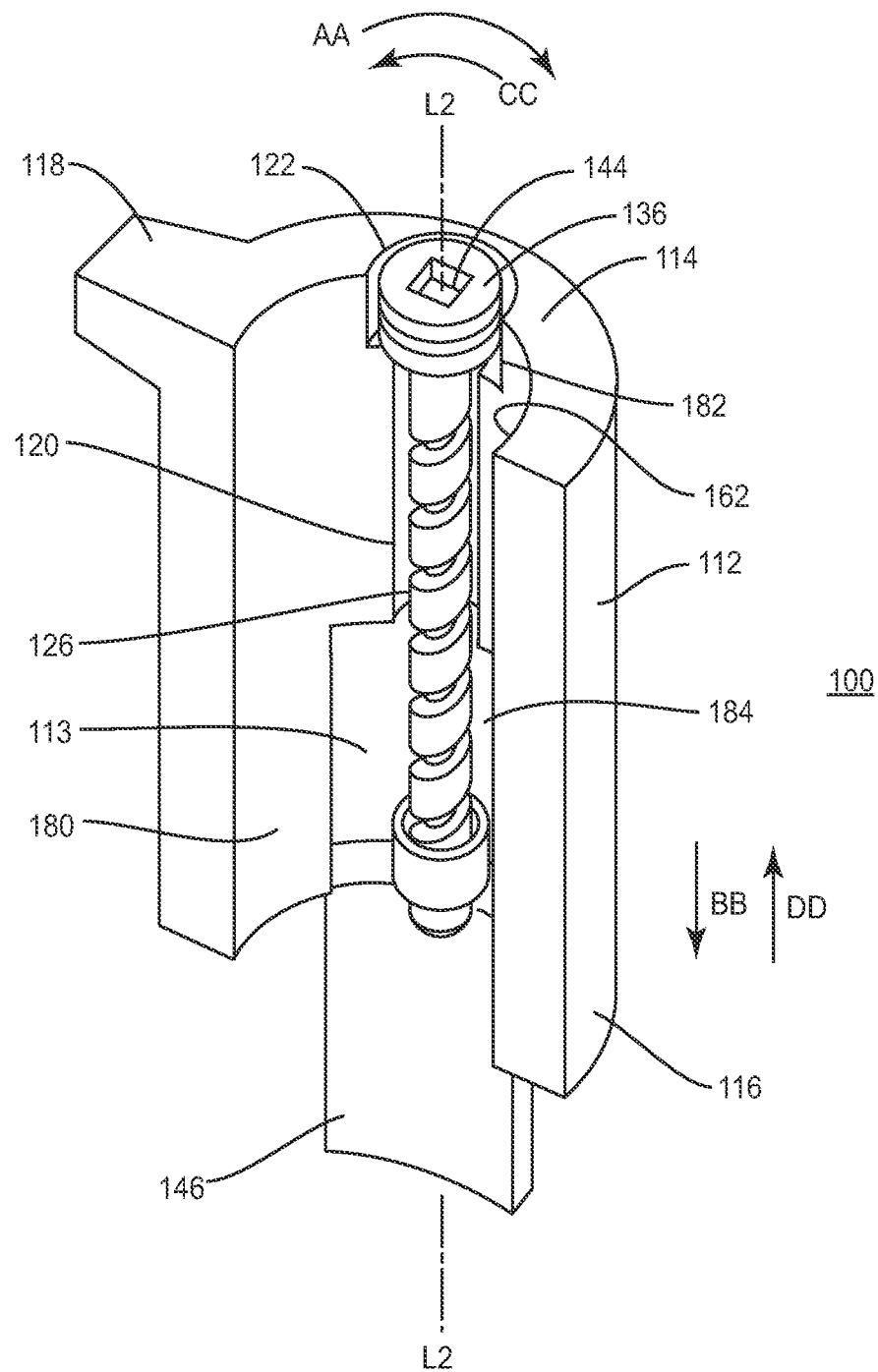
FIG. 4 is a perspective view of one embodiment of components of a system in accordance with the principles of the present disclosure.
Figure 5:
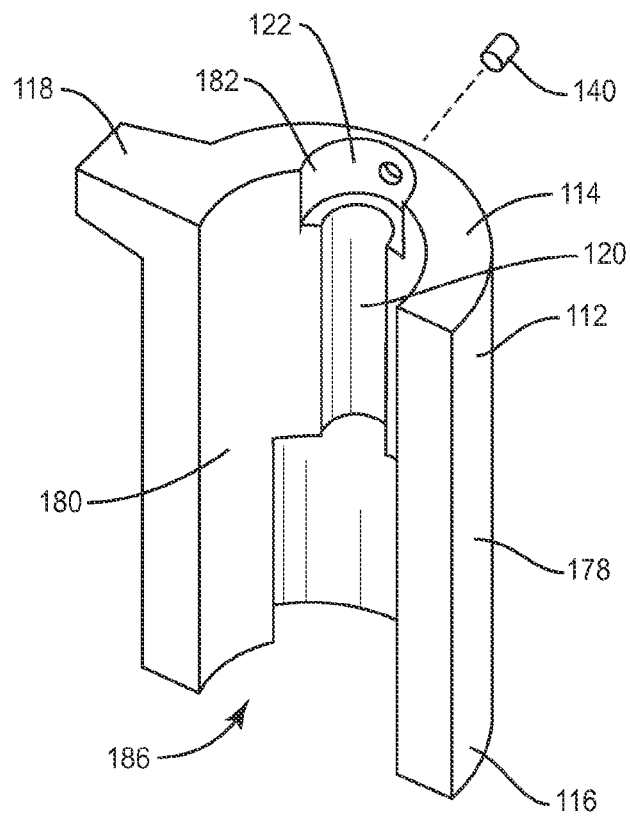
FIG. 5 is a perspective view of a component of the system shown in FIG. 4.
Figure 6:
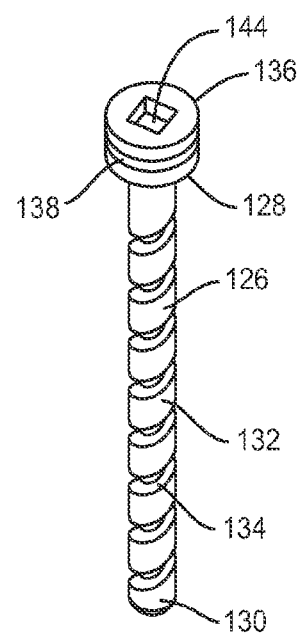
FIG. 6 is a perspective view of a component of the system shown in FIG. 4.
Figure 7:
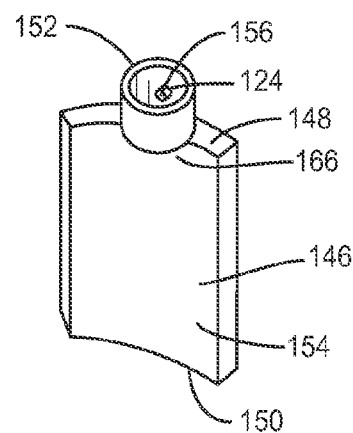
FIG. 7 is a perspective view of a component of the system shown in FIG. 4.

In one embodiment, as shown in FIGS. 4-6, surgical system 5 includes a retractor assembly 100, similar to retractor assembly 10 described above with regard to FIGS. 1-3, which includes a first wall, such as, for example, a semi-circular extension 112 extending between a first end 114 and a second end 116. First end 114 includes a base 118 configured for attachment to a retractor frame (not shown).

Extension 112 defines a longitudinal axis L2. Extension 112 includes an outer wall section 178 and an inner wall section 180. Inner wall section 180 defines an inner surface 162. Inner surface 162 defines a longitudinal cavity, such as, for example, an elongated passageway 120 configured for disposal of a shaft 126, as discussed herein. Passageway 120 extends the length of extension 112 between and/or including first end 114 and second end 116 to facilitate axial translation of blade 146 into and out of extension 112.

Extension 112 includes an interior surface 113 that defines a passageway 184. Passageway 184 is configured for axial slidable disposal of blade 146 relative to extension 112. Passageway 184 has a cross section configured to fit blade 146. As shown in FIG. 5, extension 112 comprises a semi-circular cross section. Inner section 180 defines a second cavity 122 having an inner surface 182. Second cavity 122 is disposed at first end 114 and is configured for disposal of a head 136 of shaft 126, as discussed herein.

Second end 116 defines an opening 186 that communicates with passageway 184. Opening 186 has a semi-circular cross section and is configured to facilitate extension from and/or retraction of blade 146 into passageway 184.

A rotatable shaft 126 is configured for disposal in passageway 120. Shaft 126 extends between a first end 128 and a second end 130 along longitudinal axis L2. Shaft 126 has a cylindrical cross section and includes an outer surface 132 that defines a groove 134. Groove 134 defines a helical thread form.

Shaft 126 includes head 136 disposed at first end 128 and is configured for disposal in second cavity 122. Head 136 includes a socket 144 for engagement with a tool, such as, for example, a driver, not shown, to facilitate rotation of shaft 126 in a clockwise direction, as shown by arrow AA in FIG. 4 or in a counter clockwise direction, as shown by arrow CC. Shaft 126 rotates relative to inner surface 182 to axially translate blade 146 between a first orientation and a second orientation, similar to that described herein.

A blade 146 extends between a first end 148 and a second end 150. Blade 146 is configured for axial translation along passageway 184 relative to extension 112 and shaft 126. Blade 136 includes an outer surface 166 that defines a portion of a passageway 120 configured for disposal of shaft 126. Blade 146 includes a lateral opening 124 for disposal of a pin 156 therein, as discussed herein.

A pin 156 is connected with blade 146 through lateral opening 124. Pin 156 remains fixed within opening 124 as shaft 126 rotates. As shaft rotates, groove 134 moves along pin 156 to drive pin 156 and blade 146 in an axial direction such that blade 146 translates relative to extension 112. Rotation of shaft 126 causes axial translation of blade 146 relative to extension 112 between the first orientation and the second orientation. To lock shaft 126 in place to prevent rotation, a post, such as, for example, second pin 140 is biased into engagement with groove 138 and second cavity 122. In one embodiment, pin 156 is biased into engagement with groove 134 via a spring (not shown).

In one embodiment, the first orientation includes blade 146 disposed within passageway 184. Second end 150 of blade 146 is disposed adjacent second end 116 of extension 112. Pin 156 is disposed adjacent to first end 128 of shaft 126. As shaft 126 is rotated, pin 156 moves along groove 134 such that blade 146 axially translates to one or a plurality of positions corresponding to a second orientation.

In one embodiment, the second orientation includes a configuration such that second end 150 of blade 146 extends beyond second end 116 of extension 112. First end 148 of blade 146 is disposed adjacent second end 116 of extension 112. Pin 156 is disposed adjacent to second end 130 of shaft 126. It is envisioned that blade 146 may be disposed in one or a plurality of positions extending from and relative to extension 112 in the second orientation. It is further envisioned that such position may include a range of displacement of second end 150 relative to second end 116, and/or may include increments of 1 centimeter.

In one embodiment, blade 146 is selectively positioned in the second orientation and blade 146 is locked in a selected dimension and/or distance relative to second end 116, similar to that described herein.

To extend blade 146 to one or a plurality of positions corresponding to a second orientation, a driver, not shown, is engaged with socket 144 of head 136 to rotate shaft 126 in a first direction, such as, for example, a clockwise direction, as shown by arrow AA in FIG. 4. Rotation of shaft 126 in the direction shown by arrow AA causes blade 146 to axially translate along longitudinal axis L2, in the direction shown by arrow BB. Blade 146 is selectively translatable between the first orientation and the second orientation. In the first orientation, blade 146 is disposed such that second end 150 is disposed adjacent second end 116 of extension 112. Pin 156 is disposed adjacent to second end 130 of shaft 126. As shaft 126 is rotated, pin 156 moves along groove 134 such that blade 146 axially translates to one or a plurality of positions corresponding to a selected second orientation.

Upon completion of the procedure, blade 146 is axially translatable to a position within passageway 184. Shaft 126 is rotated in a counter clockwise direction, as shown by arrow CC. Rotation of shaft 126 in the direction shown by arrow CC axially translates blade 146 in an axial direction, as shown by arrow DD. Blade 146 translates from the second orientation to the first orientation such that blade 146 is drawn within extension 112. Retractor assembly 100 is removed from the surgical site.

Figure 8:
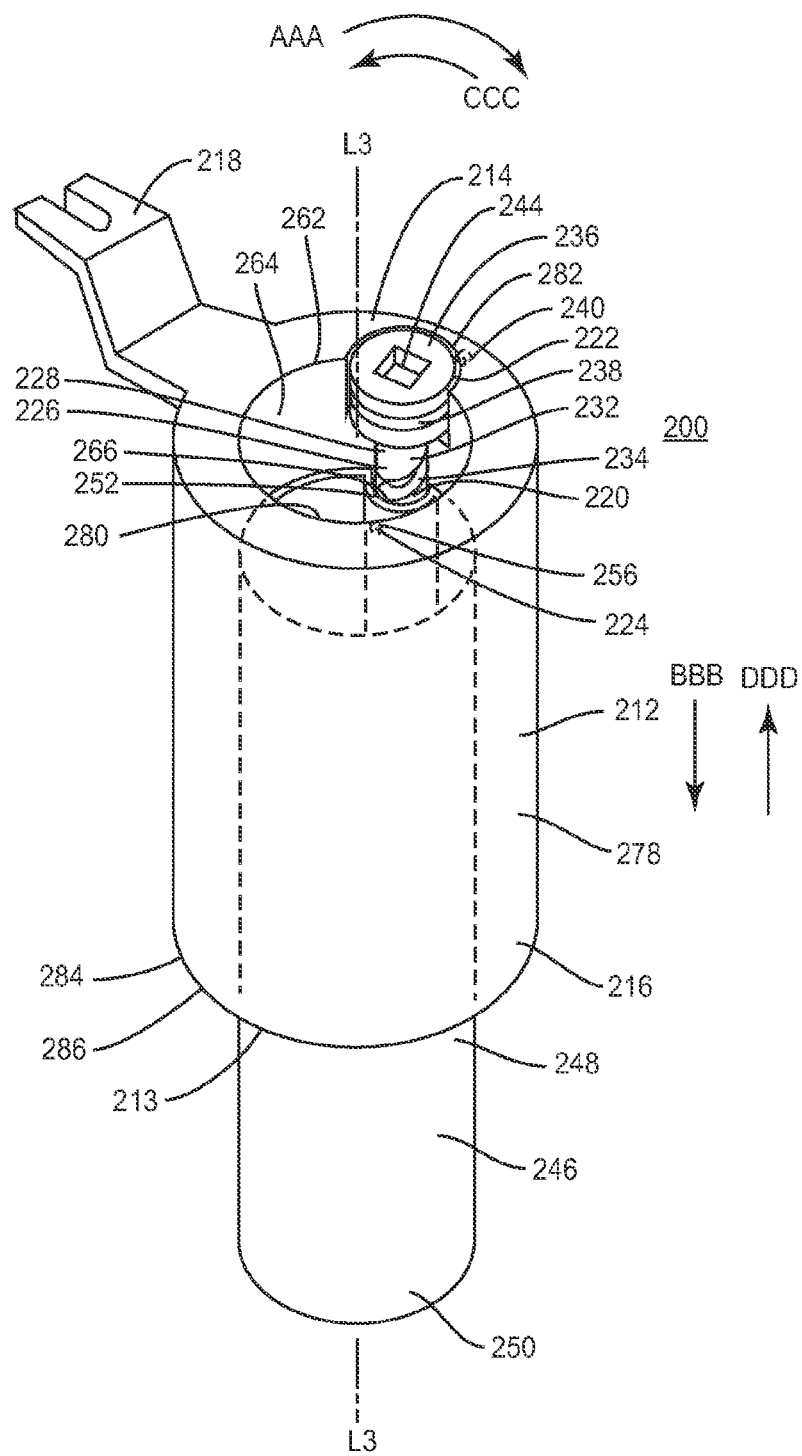
FIG. 8 is a perspective view of one embodiment of a system in accordance with the principles of the present disclosure.

In one embodiment, as shown in FIG. 8, surgical system 5 includes a retractor assembly 200, similar to the retractor assemblies described above, which includes a first wall, such as, for example, a tubular extension 212 extending between a first end 214 and a second end 216. First end 214 includes a base 218 configured for attachment to a retractor frame (not shown).

Extension 212 defines a longitudinal axis L3. Extension 212 includes an outer wall section 278 and an inner wall section 280. Inner wall section 280 defines an inner surface 262. Inner surface 262 defines a longitudinal cavity, such as, for example, an elongated passageway 220 configured for disposal of a shaft 226, as discussed herein. Passageway 220 extends the length of extension 212 between and/or including first end 214 and second end 216 to facilitate axial translation of blade 246 into and out of extension 212.

Extension 212 includes an interior surface 213 that defines a cylindrical passageway 284. Passageway 284 is configured for axial slidable disposal of a blade 246 relative to extension 212. Blade 246 has a tubular configuration and passageway 284 has a cross section configured to fit blade 246. Extension 212 comprises a semi-circular cross section. Inner section 280 defines a second cavity 222 having an inner surface 282. Second cavity 222 is disposed at first end 214 and is configured for disposal of a head 236 of shaft 226, as discussed herein.

Second end 216 defines an opening 286 that communicates with passageway 284. Opening 286 has a circular cross section and is configured to facilitate extension from and/or retraction of blade 246 into passageway 284. Extension 212 and blade 246 are disposed in alignment along a common axis, such as, for example, axis L3. Blade 246 is disposed concentrically with extension 212 and disposed for axial translation along passageway 220. It is contemplated that extension 212 and/or blade 246 may have alternate cross section configurations, such as, for example, polygonal, rectangular, oval, oblong and/or cruciate. It is further contemplated that the axes of extension 212 and blade 246 may be offset.

A rotatable shaft 226 is configured for disposal in passageway 220. Shaft 226 extends between a first end 228 and a second end (not shown) along longitudinal axis L3. Shaft 226 has a cylindrical cross section and includes an outer surface 232 that defines a groove 234. Groove 234 defines a helical thread form.

Shaft 226 includes head 236 disposed at first end 228 and is configured for disposal in second cavity 222. Head 236 includes a socket 244 for engagement with a tool, such as, for example, a driver (not shown) to facilitate rotation of shaft 226 in a clockwise direction, as shown by arrow AAA or in a counter clockwise direction, as shown by arrow CCC. Shaft 226 rotates relative to inner surface 282 to axially translate blade 246 between a first orientation and a second orientation.

A blade 246 extends between a first end 248 and a second end 250. Blade 246 is configured for axial translation along passageway 284 relative to extension 212 and shaft 226. Blade 246 includes an outer surface 266 that defines a portion of a passageway 220 configured for disposal of shaft 226. Blade 246 includes a lateral opening 224 for disposal of a pin 256 therein, as discussed herein.

A pin 256 is connected with blade 246 through lateral opening 224. Pin 256 remains fixed within opening 224 as shaft 226 rotates. As shaft 226 rotates, groove 234 moves along pin 256 to drive pin 256 and blade 246 in an axial direction such that blade 246 translates relative to extension 212. Rotation of shaft 226 causes axial translation of blade 246 relative to extension 212 between the first orientation and the second orientation. In one embodiment, pin 256 is biased into engagement with groove 234 via a spring (not shown).

To lock shaft 226 in place to prevent rotation, a second pin 240 is biased into engagement with groove 238 and second cavity 222. In one embodiment, pin 240 is spring biased into engagement with groove 238. In one embodiment, shaft 226 includes one or a plurality of cavities and/or depressions formed in a circumferential surface thereof adjacent groove 238 and configured for releasable fixation of pin 240 therewith. Fixation of pin 240 with the cavity and/or depression prevents rotation of shaft 226 to dispose blade 246 in a selected orientation.

In one embodiment, the first orientation includes blade 246 disposed within passageway 284. Second end 250 of blade 246 is disposed adjacent second end 216 of extension 212. Pin 256 is disposed adjacent to first end 228 of shaft 226. As shaft 226 is rotated, pin 256 moves along groove 234 such that blade 246 axially translates to one or a plurality of positions corresponding to a second orientation.

In one embodiment, the second orientation includes a configuration such that second end 250 of blade 246 extends beyond second end 216 of extension 212. First end 248 of blade 246 is disposed adjacent second end 216 of extension 212. Pin 256 is disposed adjacent to the second end of shaft 226. It is envisioned that blade 246 may be disposed in one or a plurality of positions extending from and relative to extension 212 in the second orientation. It is further envisioned that such position may include a range of displacement of second end 250 relative to second end 216, and/or may include increments of 1 centimeter.

In one embodiment, blade 246 is selectively positioned in the second orientation and blade 246 is locked in a selected dimension and/or distance relative to second end 216, similar to that described herein.

To extend blade 246 to one or a plurality of positions corresponding to a second orientation, a driver (not shown) is engaged with socket 244 of head 236 to rotate shaft 226 in a first direction, such as, for example, a clockwise direction, as shown by arrow AAA. Rotation of shaft 226 in the direction shown by arrow AAA causes blade 246 to axially translate along longitudinal axis L3, in the direction shown by arrow BBB. Blade 246 is selectively translatable between the first orientation and the second orientation. In the first orientation, blade 246 is disposed such that second end 250 is disposed adjacent second end 216 of extension 212. Pin 256 is disposed adjacent to the second end of shaft 226. As shaft 226 is rotated, pin 256 moves along groove 234 such that blade 246 axially translates to one or a plurality of positions corresponding to a selected second orientation.

Upon completion of the procedure, blade 246 is axially translatable to a position within passageway 284. Shaft 226 is rotated in a counter clockwise direction, as shown by arrow CCC. Rotation of shaft 226 in the direction shown by arrow CCC axially translates blade 246 in an axial direction, as shown by arrow DDD. Blade 246 translates from the second orientation to the first orientation such that blade 246 is drawn within extension 212. Retractor assembly 200 is removed from the surgical site.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A retractor comprising:
   a base;
   a first wall extending from the base, the first wall defining a longitudinal axis and extending between a first end and a second end, the first wall further defining at least a portion of a longitudinal cavity and a second cavity disposed at the first end;
   a rotatable shaft including an outer surface defining a groove, at least a portion of the shaft being disposed with the longitudinal cavity, the shaft including a head for disposal in the second cavity;
   a blade being disposed for movement along the longitudinal cavity;
   a post connected with the blade and disposed with the groove such that rotation of the shaft causes axial translation of the blade relative to the first wall between a first orientation and a second orientation, the post extending perpendicular to the longitudinal axis; and
   a cap configured to snap into engagement with a cavity in the base, the cap including a bottom surface defining a first spine surface, the head including a second spline surface that engages the first spline surface such that rotation of the shaft is prevented upon fixation of the second spline surface with the base, the cap preventing the shaft from moving proximally along the longitudinal axis.

2. The retractor as recited in claim 1 wherein the shaft includes a first lock surface engageable with a second lock surface of the first wall to releasably lock the blade in a selected dimension relative to the second end in the second orientation.

3. The retractor as recited in claim 1 wherein the blade defines a lateral opening configured for disposal of the post.

4. The retractor as recited in claim 1 wherein the blade defines a longitudinal cavity configured for disposal of the shaft, the blade being connected with the post to cause the axial translation, the longitudinal cavity of the blade being free of threads.

5. The retractor as recited in claim 1 wherein the blade includes at least one foot extending outwardly and being configured to engage tissue.

6. The retractor as recited in claim 1 wherein the retractor includes a second post and the head includes a second groove for disposal of the post to prevent axial translation of the shaft relative to the first wall, the second post extending through the first wall.

7. The retractor as recited in claim 1 wherein the head includes a socket for disposal of a tool to facilitate rotation of the shaft.

8. The retractor as recited in claim 1 wherein the post is biased for engagement with the groove by a spring.

9. The retractor as recited in claim 1 wherein the groove includes a helical pitch.

10. The retractor as recited in claim 1 wherein the groove has a linear configuration along the longitudinal axis.

11. The retractor as recited in claim 1 wherein the first wall includes an inner surface that defines an interior cavity configured for disposal of the blade.

12. A retractor comprising:
a base configured for connection with a frame;
a first wall extending from the base, the first wall defining a longitudinal axis and extending between a first end and a second end, the first wall further defining at least a portion of a first longitudinal cavity and a second cavity disposed at the first end;
a rotatable shaft including an outer surface defining a helical groove, at least a portion of the shaft being disposed with the longitudinal cavity, the shaft includes a head disposed in the second cavity;
a blade disposed for axial translation along the longitudinal cavity, the blade defining a second longitudinal cavity configured for disposal of the shaft and a lateral opening, the second longitudinal cavity being free of threads; and
a pin connected with the blade and the lateral opening and being biased for engagement with the groove by a spring such that rotation of the shaft causes axial translation of the blade relative to the first wall and the shaft between a first orientation and a second orientation such that the blade extends beyond the second end, the pin extending perpendicular to the longitudinal axis,
wherein the shaft includes a first lock surface engageable with a second lock surface of the base to releasably lock the blade in a selected dimension relative to the second end in the second orientation.

13. A retractor comprising:
a base configured for connection with a frame;
a first tubular wall extending from the base and defining an inner surface, the first wall further defining an inner cavity and a longitudinal axis and extending between a first end and a second end, the first wall further defining a longitudinal cavity recessed from the inner surface and a second cavity disposed at the first end;
a rotatable shaft including an outer surface defining a groove, at least a portion of the shaft being disposed with the longitudinal cavity, the shaft includes a head disposed in the second cavity;
a tubular blade being disposed concentrically with the first wall and disposed for axial translation along the longitudinal cavity, the blade defining an outer surface defining a second longitudinal cavity recessed from the outer surface and configured for disposal of the shaft and lateral opening, the second longitudinal cavity being free of threads; and
a pin connected with the lateral opening and biased for engagement with the groove by a spring such that rotation of the shaft causes axial translation of the blade relative to the first wall and the shaft between a first orientation and a second orientation such that the blade extends beyond the second end, the pin extending perpendicular to the longitudinal axis,
wherein the shaft includes a first lock surface engageable with a second lock surface of the base to releasably lock the blade in a selected dimension relative to the second end in the second orientation.

* * * * *

UNITED STATES PATENT AND TRADEMARK OFFICE
CERTIFICATE OF CORRECTION

| | |
|---|---|
| PATENT NO. | : 9,131,933 B2 |
| APPLICATION NO. | : 13/875036 |
| DATED | : September 15, 2015 |
| INVENTOR(S) | : Mire et al. |

It is certified that error appears in the above-identified patent and that said Letters Patent is hereby corrected as shown below:

In the Specification

In Column 7, Line 37, delete "second end 12" and insert -- second end 50 --, therefor.

In Column 9, Line 33, delete "Blade 136" and insert -- Blade 146 --, therefor.

In the Claims

In Column 12, Line 47, in Claim 1, delete "spine surface," and insert -- spline surface, --, therefor.

Signed and Sealed this
Twenty-sixth Day of April, 2016

Michelle K. Lee
*Director of the United States Patent and Trademark Office*